United States Patent
O'Neil et al.

(10) Patent No.: US 7,708,777 B2
(45) Date of Patent: May 4, 2010

(54) MODULAR INTERVERTEBRAL DISC REPLACEMENTS

(75) Inventors: Michael J. O'Neil, West Barnstable, MA (US); Jeffrey Karl Sutton, Medway, MA (US); Andrew Dooris, Raynham, MA (US)

(73) Assignee: DePuy Spine, Inc., Raynham, MA (US)

( * ) Notice: Subject to any disclaimer, the term of this patent is extended or adjusted under 35 U.S.C. 154(b) by 724 days.

(21) Appl. No.: 11/307,369

(22) Filed: Feb. 3, 2006

(65) Prior Publication Data

US 2007/0185578 A1 Aug. 9, 2007

(51) Int. Cl.
*A61F 2/44* (2006.01)
(52) U.S. Cl. .............. 623/17.14; 623/17.15; 623/17.13
(58) Field of Classification Search .... 623/17.11–17.16
See application file for complete search history.

(56) References Cited

U.S. PATENT DOCUMENTS

| | | | |
|---|---|---|---|
| 5,401,269 A | | 3/1995 | Buttner-Janz et al. |
| 5,556,431 A | * | 9/1996 | Buttner-Janz ............ 623/17.15 |
| 6,368,350 B1 | * | 4/2002 | Erickson et al. .......... 623/17.14 |
| 6,936,071 B1 | * | 8/2005 | Marnay et al. ........... 623/17.15 |
| 7,204,852 B2 | * | 4/2007 | Marnay et al. ........... 623/17.16 |
| 7,250,060 B2 | * | 7/2007 | Trieu ...................... 623/17.15 |
| 2004/0133278 A1 | * | 7/2004 | Marino et al. ............ 623/17.14 |
| 2004/0133281 A1 | | 7/2004 | Khandkar et al. |
| 2004/0143332 A1 | * | 7/2004 | Krueger et al. ........... 623/17.14 |
| 2004/0172021 A1 | | 9/2004 | Khalili |
| 2005/0277938 A1 | | 12/2005 | Parsons |

FOREIGN PATENT DOCUMENTS

| | | |
|---|---|---|
| EP | 1374808 | 1/2004 |
| WO | WO-2004/054480 | 7/2004 |

\* cited by examiner

*Primary Examiner*—Pedro Philogene
(74) *Attorney, Agent, or Firm*—Nutter McClennen & Fish LLP (57) ABSTRACT

A modular disc prosthesis system is provided that allows a disc prosthesis to be constructed, either pre- or intra-operatively, to have a desired degree of freedom or constraint when positioned between endplates of adjacent vertebrae. In particular, the components can be assembled to form a disc prosthesis having a center of rotation that is constrained or fixed such that, when the disc prosthesis is implanted between endplates of adjacent vertebrae, the adjacent vertebrae have one degree of freedom and move about a fixed center of rotation. Alternatively, one or more of the same components and one or more additional components of the system can be used to construct a disc prosthesis having a center of rotation that is unconstrained or that floats such that, when the disc prosthesis is implanted between the endplates of adjacent vertebrae, the adjacent vertebrae have multiple degrees of freedom and can move about a floating or moving center of rotation, i.e., a center of rotation that is not fixed.

27 Claims, 8 Drawing Sheets

MODULAR INTERVERTEBRAL DISC REPLACEMENTS

FIELD OF THE INVENTION

The present invention relates to intervertebral disc replacement devices, and methods for implanting intervertebral disc replacement devices.

BACKGROUND OF THE INVENTION

Advancing age, as well as injuries, can lead to changes in the various bones, discs, joints and ligaments of the body. In particular, these changes can manifest themselves in the form of damage or degeneration of an intervertebral disc, the result of which is mild to severe chronic back pain. Intervertebral discs serve as "shock" absorbers for the spinal column, absorbing pressure delivered to the spinal column. Additionally, they maintain the proper anatomical separation between two adjacent vertebra. This separation is necessary for allowing both the afferent and efferent nerves to exit and enter, respectively, the spinal column.

Treatment for a diseased or damaged disc can involve the removal of the affected disc and subsequent fusion of the opposing vertebra to one another. Spinal fusion consists of fusing the adjacent vertebrae through the disc space (the space previously occupied by the spinal disc interposed between the adjacent vertebral bodies). Typically, a fusion cage and/or bone graft is placed into the disc space to position the vertebrae apart so as to create more space for the nerves, to restore the angular relationship between the adjacent vertebrae to be fused, and to provide for material that can participate in and promote the fusion process.

More recently, spinal prostheses have been developed that allow one or more degrees of freedom between the adjacent vertebrae, thereby restoring function to the vertebrae. One well known spinal prosthesis is the CHARITÉ® produced by DePuy Spine, Inc. of Raynham, Mass., which includes two metal endplates and a center polyethylene core. The center core includes superior and inferior spherical bearing surfaces that are received within concave surfaces formed in the superior and inferior endplates. Once implanted, the prosthesis will allow multiple degrees of freedom between the endplates of the adjacent vertebrae. Other prostheses are known having a semi-constrained configuration, allowing minimal degrees of freedom between the endplates of the vertebrae, or a constrained configuration, allowing only one degree of freedom between the endplates of the vertebrae.

The particular level of laxity or constraint needed can vary depending on the patient's condition. For instance, a patient with symptomatic or suspect disc at the neighboring level may be better served with a less constrained device, like the CHARITÉ®. Conversely, a surgeon may select to implant a prosthesis with less laxity to limit motion due to the patient's facet condition at the operative level, as might be the case for an older patient with less activity.

While prostheses having various degrees of freedom are known in the art, no one prosthesis allows a surgeon with the flexibility to select the degree of constraint either pre- or intra-operatively based upon the patients sagittal and/or coronal alignment, facet and/or annulus condition, neighboring level condition, as well as various other factors. Accordingly, there remains a need for a disc prosthesis system which allows for greater modularity, and in particular which allows a surgeon to construct a prosthesis having a desired degree of freedom.

SUMMARY OF THE INVENTION

The present invention provides modular intervertebral disc prosthesis systems having multiple components which can be used to construct a prosthesis having a desired degree of freedom or constraint. In one exemplary embodiment, a modular intervertebral disc prosthesis system is provided and includes a plurality of modular components with at least three of the modular components being adapted to couple to one another to form a disc replacement configured to be disposed between adjacent superior and inferior vertebrae. The components can be configured to selectively form a first disc replacement having a fixed center of rotation, or a second disc replacement having a floating center of rotation. In an exemplary embodiment, the components include a core component and a plurality of interchangeable components adapted to movably couple to the core component. At least one of the interchangeable components can be configured to movably couple to the core component to form a disc prosthesis having a fixed center of rotation, and at least another one of the interchangeable components can be configured to movably couple to the core component to form a disc prosthesis having a floating center of rotation.

While the core component can have a variety of configurations, in one exemplary embodiment the core component is in the form of a first endplate component that is adapted to be positioned adjacent to a vertebral endplate. The interchangeable components can include a second endplate component that is adapted to be positioned adjacent to an endplate of a vertebra, and a plurality of central components that are adapted to be movably disposed between the first and second endplate components. In an exemplary embodiment, the second endplate component can include a bone-contacting surface adapted to be positioned adjacent to an endplate of a vertebra, and an opposed mating surface adapted to mate to at least one of the various central components.

The central components can also vary, and in one embodiment the system can include first and second central components that are adapted to be movably disposed between the first and second endplate components to form a disc prosthesis having a floating center of rotation. The first central component can include a first substantially convex surface that is adapted to be movably seated within a corresponding substantially concave surface formed in the first endplate component, and an opposed substantially convex surface adapted to be movably seated within a corresponding substantially concave surface formed in the second component. The second central component can be adapted to mate to the second endplate component, using, for example, a snap-fit connection, an interference fit connection, a tongue-and-groove connection, a post-and-bore connection, and/or a press-fit connection.

The system can also include a third central component that is interchangeable with the first and second central components, and that is adapted to be movably disposed between the first and second endplate components to form a disc prosthesis having a fixed center of rotation. The third central component can include a substantially convex surface that is adapted to be received within a corresponding substantially concave surface formed in the first endplate component, and an opposed mating surface that is adapted to mate to a complementary mating surface formed on the second endplate component. The third central component and the second endplate component can mate using, for example, a snap-fit connection, an interference fit connection, a tongue-and-groove connection, a post-and-bore connection, and/or a press-fit connection.

In another embodiment, the interchangeable components can include a second endplate component and a third endplate component that are interchangeable, and that are adapted to be positioned adjacent to an endplate of a vertebra. A plurality of central components can be adapted to be movably disposed between the first endplate component and one of the second and third endplate components. In an exemplary embodiment, the second endplate component can include a bone-contacting surface adapted to be positioned adjacent to an endplate of a vertebra, and an opposed surface having a substantially convex cavity formed therein, and the third endplate component can include a bone-contacting surface adapted to be positioned adjacent to en endplate of a vertebra, and an opposed mating surface adapted to mate to at least one of the plurality of central components.

In yet another embodiment, the central components can include a first central component that is adapted to be movably disposed between the first and second endplate components, and a second central component that is adapted to be disposed between the first and second components, and that is adapted to move relative to the first component and to mate to the second component to prevent movement between the second central component and the second endplate component. Various techniques can be used to mate the second central component and the second endplate component. For example, the second central component can include an undercut formed around a perimeter thereof and adapted to receive and engage a corresponding ridge formed on the second endplate component to prevent movement between the second central component and the second endplate component. In another embodiment, the second central component can include a plurality of protrusions formed thereon and adapted to extend into and engage corresponding bores formed in the second endplate component to prevent movement between the second central component and the second endplate component. In yet another embodiment, the second central component can be adapted to rotate into a locked position to engage the second endplate component to prevent movement between the second central component and the second endplate component.

In yet another embodiment, a modular disc prosthesis kit is provided having at least three components adapted to couple to one another to form a first disc replacement configured to be disposed between adjacent superior and inferior vertebrae and having a constrained center of rotation, and at least one interchangeable component adapted to replace at least one of the at least three components to form a second disc replacement having an unconstrained center of rotation. In an exemplary embodiment, the components include a first endplate component that is adapted to be positioned adjacent to a first endplate of a first vertebra, a second endplate component that is adapted to be positioned adjacent to a second endplate of an adjacent second vertebra, and a plurality of cores that are adapted to be interchangeably disposed between the first and second endplate components to allow a first disc prosthesis to be formed having a constrained center of rotation, and a second disc prosthesis to be formed having unconstrained center of rotation. In one embodiment, the plurality of cores can include a first core that is adapted to be freely movably disposed between the first and second endplate components, and a second core that is adapted to be disposed between the first and second endplate components and that is adapted to move freely relative to the first endplate component and to engage the second endplate component to prevent movement between the second core and the second endplate component. In yet another embodiment, the plurality of cores can include first and second cores that are adapted to be movably disposed between the first and second endplate components to form a disc prosthesis having an unconstrained center of rotation, and a third core that is adapted to be disposed between the first and second endplate components to form a disc prosthesis having a constrained center of rotation. In an exemplary embodiment, the first core can have a post formed thereon for mating with a bore formed in the second endplate component, and a substantially concave surface for seating a complementary substantially convex surface formed on the second core, and the third core can have a post formed thereon for mating with a bore formed in the second endplate component, and a substantially convex surface adapted to be movably received within a complementary concave surface formed in the first endplate component.

BRIEF DESCRIPTION OF THE DRAWINGS

The invention will be more fully understood from the following detailed description taken in conjunction with the accompanying drawings, in which.

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention provides a modular disc prosthesis system that allows a disc prosthesis to be constructed, either pre- or intra-operatively, to have a desired degree of freedom or constraint when positioned between endplates of adjacent vertebrae. For example, the components can be assembled to form a disc prosthesis having a center of rotation that is constrained or fixed such that, when the disc prosthesis is implanted between endplates of adjacent vertebrae, the adjacent vertebrae have one degree of freedom and move about a fixed center of rotation. Thus, the disc prosthesis can allow flexion, extension, and lateral bending about a fixed center of rotation. The disc prosthesis can also optionally allow axial rotation of the adjacent vertebrae about the fixed center of rotation. Alternatively, one or more of the same components and one or more additional components of the system can be used to construct a disc prosthesis having a center of rotation that is unconstrained or that floats such that, when the disc prosthesis is implanted between the endplates of adjacent vertebrae, the adjacent vertebrae have multiple degrees of freedom and can move about a floating or moving center of rotation, i.e., a center of rotation that is not fixed. Thus, the disc prosthesis can allow flexion, extension, lateral bending, axial rotation, anterior-posterior shear or translation, and medial-lateral shear or translation about a floating or moving center of rotation. In certain exemplary embodiments, the modular disc prosthesis system can also be configured to facilitate optimal positioning of the center of rotation of the prosthesis relative to the endplates of the adjacent vertebrae, as will be discussed in more detail below.

FIGS. 1A-2C illustrate one exemplary embodiment of a modular disc prosthesis system having various components that can be combined to selectively form a constrained (fixed center of rotation) or an unconstrained (floating center of rotation) disc prosthesis. In general, the modular disc prosthesis system includes a core component and various interchangeable components which can be used with the core component to construct either a constrained prosthesis or an unconstrained prosthesis. While the core component can vary, in the illustrated embodiment the core component is in the form of a first endplate component 10, shown in FIG. 1A. The first endplate component 10 can have a variety of shapes and sizes, but it is preferably adapted to be positioned adjacent to a vertebral endplate. Accordingly, in certain exemplary embodiments, the first endplate component 10 can have a size and shape that complements that size and shape of a vertebral endplate. Other shapes include, by way of non-limiting example, circular, rectangular, square, trapezoidal, oblong, square or trapezoidal with rounded corners, elliptical, kidney bean shaped, etc. The first endplate component 10 can also include features to facilitate attachment or positioning of the first endplate component 10 adjacent to the endplate of a vertebrae. For example, a bone-contacting surface 12 of the first endplate component 10 can include bone-engaging surface features (not shown), such as teeth, formed thereon for engaging the vertebral endplate and preventing movement of the first endplate component relative to the vertebra. The endplate components can also or alternatively include a coating disposed thereof, such as plasma sprayed titanium, porous sintered metal beads, hydroxyapatite, or calcium phosphate, to facilitate positioning and engagement with the vertebral endplate. The first endplate component 10 can also include a second surface 14, opposed to the bone-contacting surface, for coupling to or seating one of the interchangeable components. While the configuration of the second surface 14 will vary depending on the configuration of the interchangeable components, in an exemplary embodiment the second surface 14 is an articular surface for seating a complementary articular surface formed on an interchangeable component. In the illustrated embodiment, the second articular surface 14 includes a substantially concave spherical cavity 16 formed therein and adapted to receive a complementary substantially convex spherical surface formed on an interchangeable component.

Figure 1A:
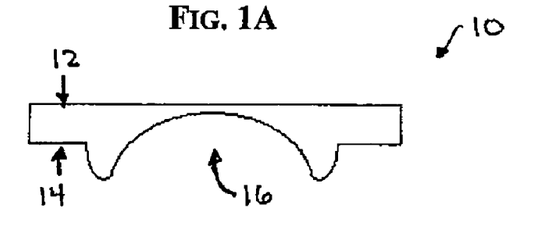
FIG. 1A is a cross-sectional side view of a first endplate component of one embodiment of a modular disc prosthesis system.
Figure 1B:
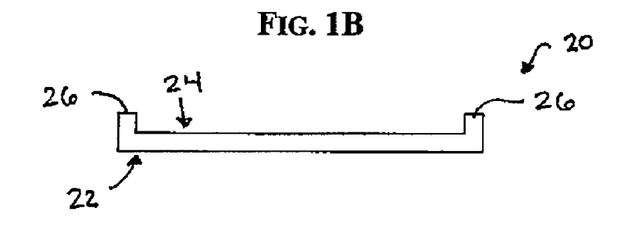
FIG. 1B is a cross-sectional side view of a second endplate component for use with the first endplate component shown in FIG. 1A.

The interchangeable components can also have a variety of configurations, and the system can include any number of interchangeable components. In an exemplary embodiment, the system includes at least one second endplate component, and multiple central components configured to be positioned between the first endplate component 10 and one of the second endplate components. FIG. 1B illustrates one exemplary embodiment of a second endplate component 20, which generally includes a bone-contacting surface 22, that can be similar to the bone-contacting surface 12 on the first endplate component, and an opposed mating surface 24. The mating surface 24 can have various configurations, but it is preferably adapted to mate to a central component. Exemplary mating techniques will be discussed in more detail below. The shape and size of the second endplate component 20 can vary, and it can have a shape and size that complements the shape and size of an endplate of a vertebra. As shown in FIG. 1B, the second endplate component 20 has a plate-like configuration with a raised perimeter edge 26 formed therearound for receiving a central component. The second endplate component 20 can also include features, such as teeth and/or coatings, to facilitate attachment or positioning relative to a vertebral endplate, as previously discussed above with respect to the first endplate component 10.

Figure 1C:
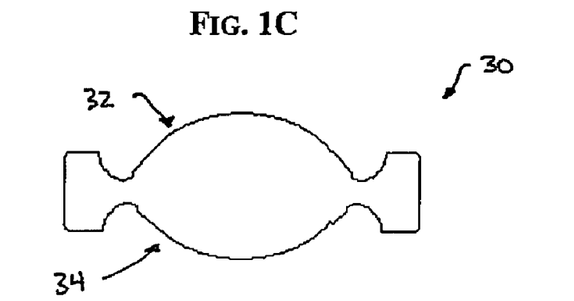
FIG. 1C is a side view of a first central component for use with the first and second endplate components shown in FIGS. 1A and 1B.

As previously indicated, the system can also include multiple central components that are configured to be positioned between the first and second endplate components 10, 20. In an exemplary embodiment, the system includes one or more central components that are configured to be positioned between the first and second endplate components 10, 20 to form a disc prosthesis having a floating center of rotation, and one or more additional central components that are configured to be positioned between the first and second endplate components 10, 20 to form a disc prosthesis having a fixed center of rotation. FIGS. 1C and 1E illustrate one exemplary embodiment of first and second central components 30, 50 that work together with the first and second endplate components 10, 20 to form a disc prosthesis having a floating center of rotation, and FIG. 1E illustrates one exemplary embodiment of third central component 40 that works with the first and second endplate components 10, 20 to form a disc prosthesis having a fixed center of rotation.

Turning first to FIG. 1C, a first central component 30 is shown having opposed articular surfaces 32, 34. While the shape of the articular surfaces 32, 34 can vary, in the illustrated embodiment each surface 32, 34 has a substantially spherical convex shape. The first convex surface 32 is configured to be received within the substantially concave cavity 16 formed in the second surface 14 of the first endplate component. The second convex surface 34 on the first central component 30 is configured to be received within a complementary cavity. Since the second endplate component 20 does not include a complementary cavity formed therein, the second central component 50, shown in FIG. 1E, can be used to allow movement between the first central component 30 and the second endplate component 20. As shown the second central component 50 includes a first surface 52 having a substantially concave cavity 56 formed therein for seating the convex surface 34 on the first central component 30, and an opposed second surface 54 that is adapted to mate to the mating surface 24 on the second endplate component 20. Exemplary mating techniques for mating the second central component 50 and the second endplate component 20 will be discussed in more detail below.

Figure 2A:
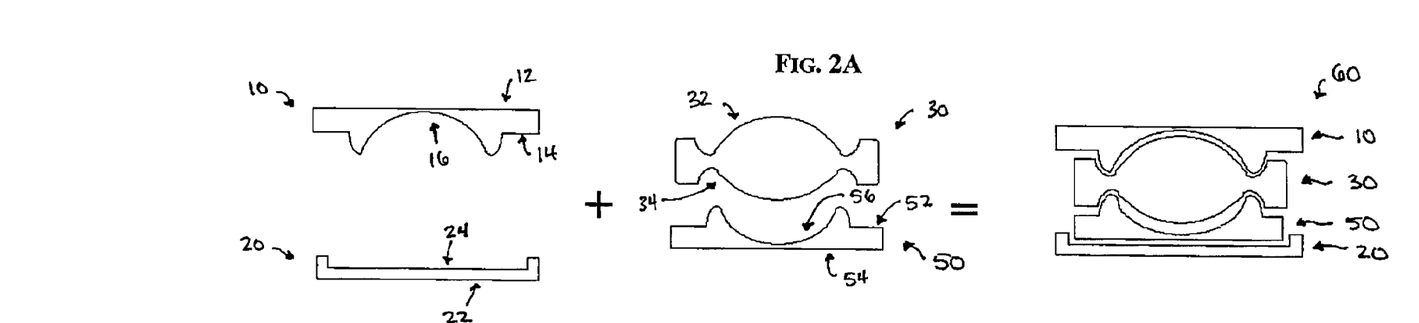
FIG. 2A is a cross-sectional side view of the first endplate component of FIG. 1A, the second endplate component of FIG. 1B, and the central component of FIG. 1C coupled to form a first disc prosthesis having a floating center of rotation.

In use, the first central component 30 is positioned to seat the convex surface 34 within the concave cavity 56 on the second central component 50, and the two components 30, 50 are positioned between the first and second endplate components 10, 20 to form a disc prosthesis 60 having a floating center of rotation, as shown in FIG. 2A. In particular, the mating surface 54 on the second central component 50 is mated to the mating surface 24 on the second endplate component 20, and the convex surface 32 on the first central component 30 is seated within the concave cavity 16 formed in the first endplate component 10. The endplate components 10, 20 will be fixed relative to the adjacent vertebrae, however the spherical convex surfaces 32, 34 on the first central component 30 will allow the endplate components 10, 20, and thus the adjacent vertebrae, to move relative to one another about a center of rotation that floats. In other words, since the first central component 30 is not fixedly attached to either endplate component 10, 20 and is free to move between the adjacent vertebrae, the adjacent vertebrae have multiple degrees of freedom.

Figure 1D:
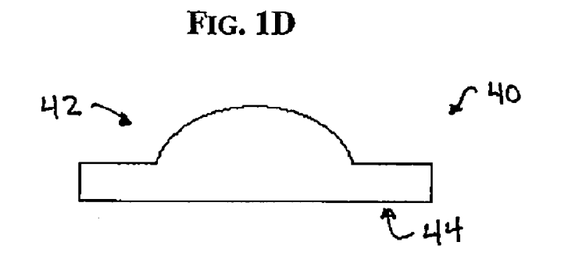
FIG. 1D is a cross-sectional side view of a second central component for use with the first and second endplate components shown in FIGS. 1A and 1B.
Figure 1E:
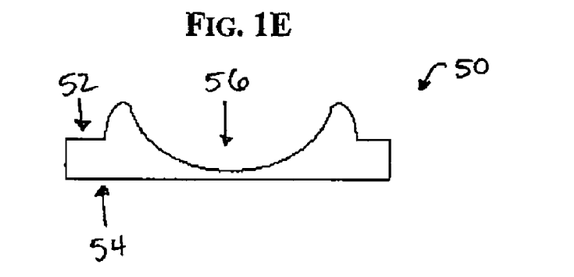
FIG. 1E is a cross-sectional side view of a second endplate component for use with the first endplate component of FIG. 1A and the central first central component of FIG. 1C.

As discussed above, a third central component 40, shown in FIG. 1D, can be used instead of the first and second central components 30, 50, to form a disc prosthesis having a fixed center of rotation. The third central component 40 can have a variety of configurations, but in an exemplary embodiment it includes a first articular surface 42, which can have a substantially spherical convex shape that is adapted to be received within the substantially spherical concave cavity 16 formed in the first endplate component 10. The third central component 40 can also include an opposed mating surface 44 that is adapted to mate to the mating surface 24 on the second endplate component 20. Various exemplary techniques for mating the third central component 40 to the second endplate component 20 will be discussed in more detail below.

Figure 2B:
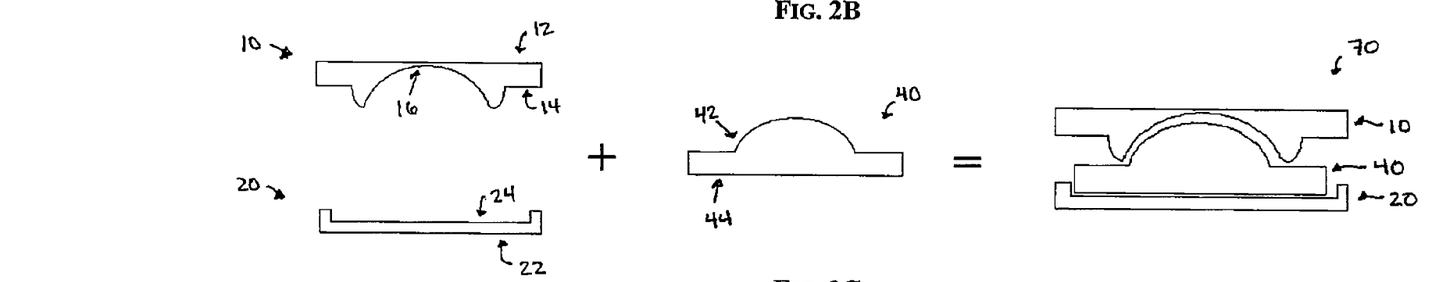
FIG. 2B is a cross-sectional side view of the first endplate component of FIG. 1A, the second endplate component of FIG. 1B, and the central component of FIG. 1D coupled to form a second disc prosthesis having a fixed center of rotation.

In use, as shown in FIG. 2B, the third central component 40 is positioned between the first and second endplate components 10, 20 to form a disc prosthesis 70 having a fixed center of rotation. In particular, the spherical convex articular surface 42 on the third central component 40 is received within the convex surface 16 on the first endplate component 10, and the mating surface 44 on the third endplate component 40 is mated to the mating surface 24 on the second endplate component 20. Since the third central component 40 is fixed relative to the second endplate component 20, movement can only occur between the first endplate component 10 and the third central component 40. Thus, the adjacent vertebrae coupled to the endplate components 10, 20 have one degree of freedom and can only move about a substantially fixed center of rotation.

Figure 2C:
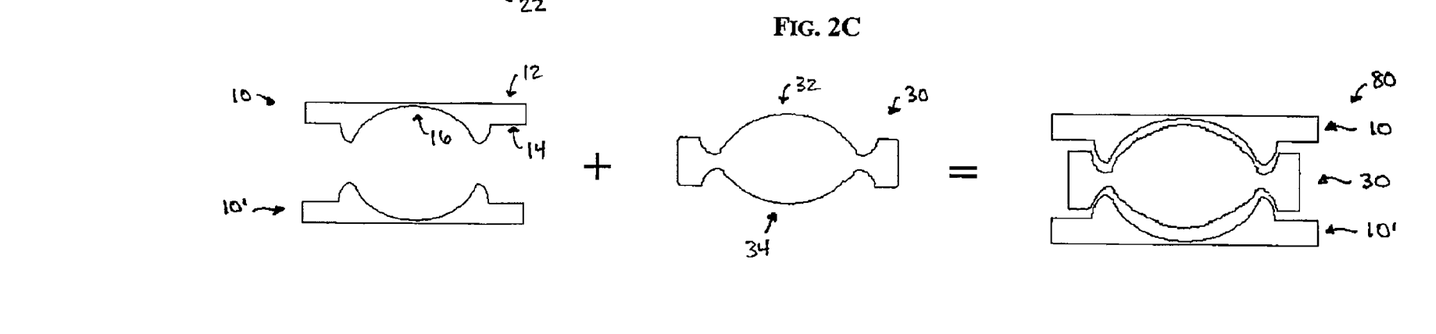
FIG. 2C is a cross-sectional side view of the first endplate component of FIG. 1A, the second endplate component of FIG. 1D, and the central component of FIG. 1C coupled to form a third disc prosthesis having a floating center of rotation.

In other embodiments, as shown in FIG. 2C, a disc prosthesis having a floating center of rotation can be formed using only three components, rather than four components as shown in FIG. 2A. In particular, the second central component 50 and the second endplate component 20 can be replaced by an endplate component 10', as shown in FIG. 2C, to form a disc prosthesis 80. Endplate component 10' can have a configuration similar to the first endplate component 10.

Figure 3A:
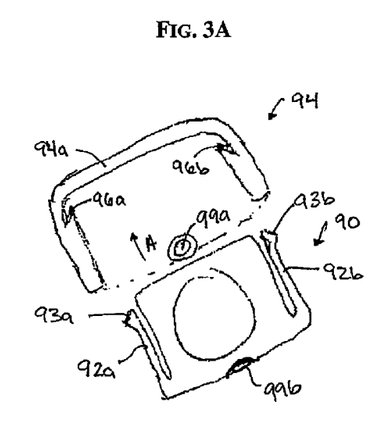
FIG. 3A is a top view of one embodiment of a technique for mating two modular components.
Figure 3B:
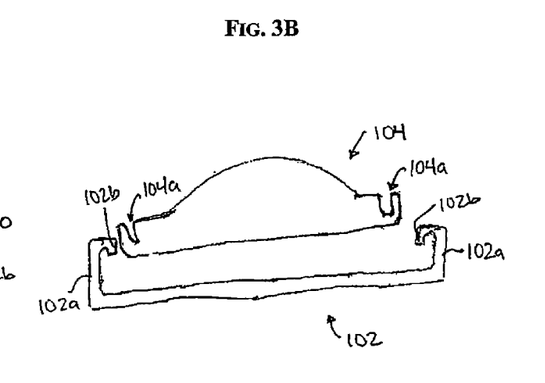
FIG. 3B is a cross-sectional side view of another embodiment of a technique for mating two modular components.
Figure 3C:
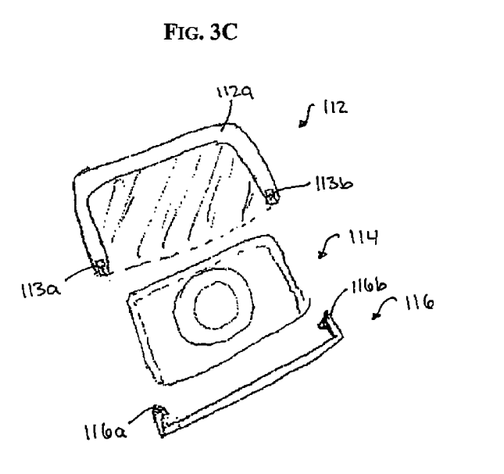
FIG. 3C is a top view of another embodiment of a technique for mating two modular components.

As previously indicated, various techniques can be used to mate the second and third central components 50, 40 to the second endplate component 20. FIGS. 3A-3C illustrate various exemplary mating techniques for mating two components. A person skilled in the art will appreciate that, while particular components are shown, the various mating techniques can be used with any two components that need to be mated to one another.

In the embodiment shown in FIG. 3A, the components are configured to slidably mate and snap into one another. In particular, FIG. 3A illustrates a first component 90 having deflectable arms 92a, 92b formed on opposed sides thereof. The arms 92a, 92b on the first component 90 can extend adjacent to opposed sides of the first component 90, and they can be attached to the component 90 at one end thereof such that the arms 92a, 92b can deflect inward toward the opposed sides of the first component 90. A terminal end of each arm 92a, 92b can include a protrusion 93a, 93b formed thereon. FIG. 3A also illustrates a second component 94 having detents 96a, 96b for receiving the protrusions 93a, 93b on the opposed arms 92a, 92b. The detents 96a, 96b in the second component 94 can be formed in opposed sidewalls of a raised perimeter edge 94a that extends around at least a portion of a perimeter of the second component 94. In use, the first component 90 is slid into the second component 94 in a direction indicated by arrow A. As a result, the raised perimeter edge 94a on the second component 94 will cause the arms 92a, 92b to deflect inward until the protrusions 93a, 93b on the arms 92a, 92b snap into and engage the detents 96a, 96b in the second component 94, thereby locking the first component 90 within the second component 94. While the deflectable arms 92a, 92b can be sufficient to retain the first component 90 within the second component 94, the components can also optionally include bores 99a, 99b formed therein for receiving a set screw to threadably mate the first and second components 90, 94. A person skilled in the art will appreciate that the protrusions 93a, 93b and detents 96a, 96b can be formed at various locations on the first and second components 90, 94, and that they can have a variety of other configurations.

FIG. 3B illustrates another embodiment of a technique for mating two components. In this embodiment, the mating connection is similar to that shown in FIG. 3A in that the components snap onto one another. However, rather than sliding the first component into the second component, in this embodiment the components mate using a top-loading technique. In particular, FIG. 3B illustrates a first component 102 having a raised perimeter edge or sidewall 102a formed around at least a portion of a perimeter thereof (only a cross-section of the sidewall 102a is shown). The sidewall includes a tongue or hook-shaped member 102b formed thereon and configured to engage the second component 104. The second component 104 includes a complementary groove 104a formed around at least a portion of a perimeter thereof (only a cross-section of the groove 104a is shown) for seating the tongue or hook-shaped member 102b on the first component 102. In use, the second component 104 is top-loaded into the first component 102 until the hook-shaped member 102b on the first component 102 engages and extends into the groove 104a formed in the second component 104, thereby mating the two components 102, 104. Manual force or an impacting force can be used to insert the second component 104 into the first component 102. A person skilled in the art will appreciate that the tongue-and-groove mating connection can be formed at a variety of locations on the components, and can have a variety of other configurations.

FIG. 3C illustrates yet another embodiment of a mating technique for mating two components of a modular disc replacement system. In this embodiment, two components 112, 114 slidably mate to one another, and a clip 116 is used to secure the components. In particular, the first component 112 includes a raised perimeter edge or sidewall 112a formed around a portion of a perimeter thereof, and opposed ends of the sidewall 112a include a mating element, such as a bore 113a, 113b, formed therein. The second component 114 is merely configured to be received within the sidewall 112a of the first component 112. The clip 116 is configured to couple to and extend between the opposed ends of the sidewall 112a. The clip 116 can thus include a mating element, such as a post or protrusion 116a, 116b, formed on each end thereof for extending into and mating with the bores 113a, 113b formed in each end of the sidewall 112a of the first component 112. In an exemplary embodiment, the posts 116a, 116b are configured to snap-into or be press-fit into the bores 113a, 113b. In use, the second component 114 is positioned on top of the first component 112 and within the sidewalls 112a of the first component 112, and the clip 116 is mated to the opposed ends of the sidewall 112a of the first component 112. As a result, the clip 116 will extend across a portion of the second component 114, thereby retaining the second component 114 within the first component 112. The first and second components 112, 114 can also optionally include a tongue-and-groove connection, as described above with respect to FIG. 3B, to further retain the second component 114 within the first component 112.

Figure 4A:
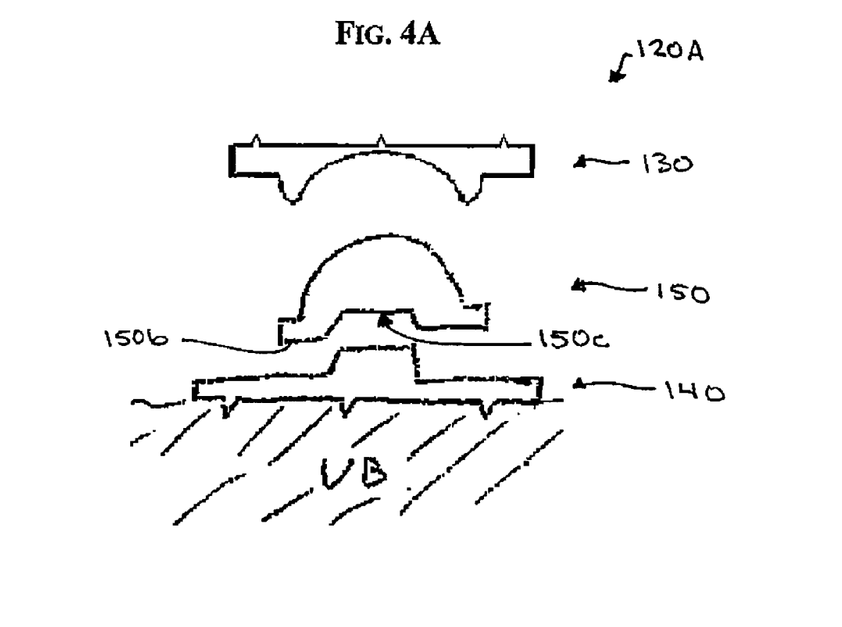
FIG. 4A is a cross-sectional side view of another embodiment of a modular disc prosthesis system having first and second endplate components, and a central component for forming a modular disc prosthesis having a fixed center of rotation.
Figure 4B:
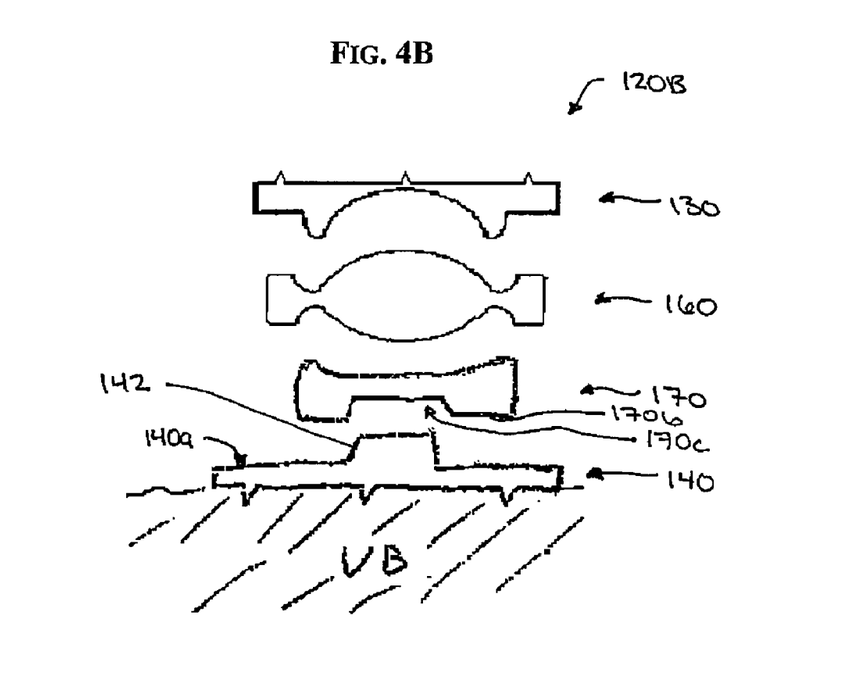
FIG. 4B is a cross-sectional side view of the first and second endplate components shown in FIG. 4A, and another embodiment of a central component for forming a modular disc prosthesis having a floating center of rotation.

FIGS. 4A-4B illustrate an additional embodiment of technique for mating an endplate component and a central component. In this embodiment, the modular disc replacement system is similar to the modular disc replacement system previously described with respect to FIGS. 1A-2C. In particular, the system in FIGS. 4A and 4B includes first and second endplate components 130, 140, a first central component 150 that is disposed between the first and second endplate components 130, 140 to form a disc prosthesis 120A having fixed center of rotation, and second and third central components 160, 170 that are disposed between the first and second endplate components 130, 140 to form a disc prosthesis 120B having a floating center of rotation. Unlike the embodiment shown in FIGS. 1A-2C, however, the system shown in FIGS. 4A-4B uses a post-and-bore connection to mate the first and second central components 150, 170 to the second endplate component 140. In particular, the second endplate component 140 has a mating surface 140a with a post 142 formed thereon and configured to extend into a complementary bore 150c formed in a mating surface 150b of the first central component 150, and a complementary bore 170c formed in a mating surface 170b of the third central component 170. The post 142 can have a variety of shapes and sizes. For example, the post 142 can be conical, cylindrical, square, rectangular, etc. The particular configuration of the post 142 can also be determinative of the type of movement allowed between the central component and the second endplate component 140. For example, a conical or cylindrical post will allow rotation between the central component and the second endplate component, whereas a non-symmetrical post will prevent rotation between the two components. The post and bore can also have a shape that limits an orientation in which the endplate component and the central component mate to one another. In one exemplary embodiment, the post and bore can each have a rectangular shape. In use, the offset position of the post will allow optimal positioning of a center of rotation of the prosthesis relative to the endplates of the adjacent vertebrae.

Figure 5A:
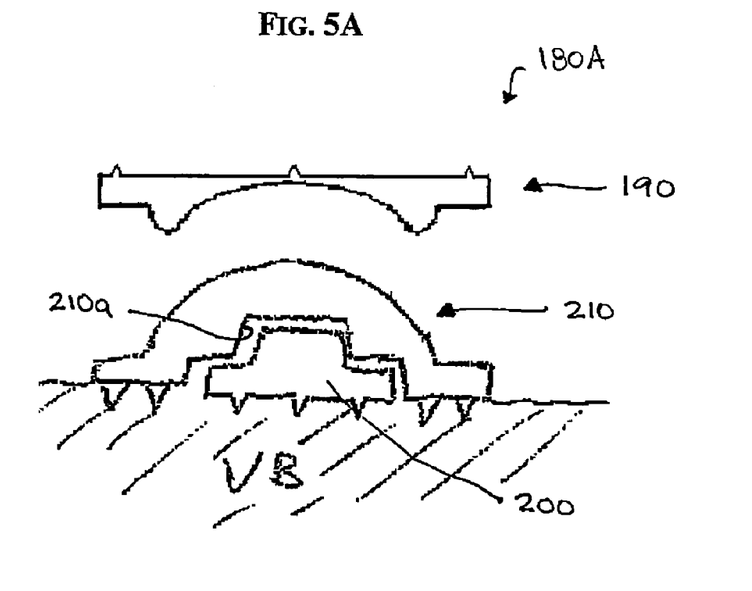
FIG. 5A is a cross-sectional side view of yet another embodiment of a modular disc prosthesis system having first and second endplate components, and a central component for forming a modular disc prosthesis having a fixed center of rotation.
Figure 5B:
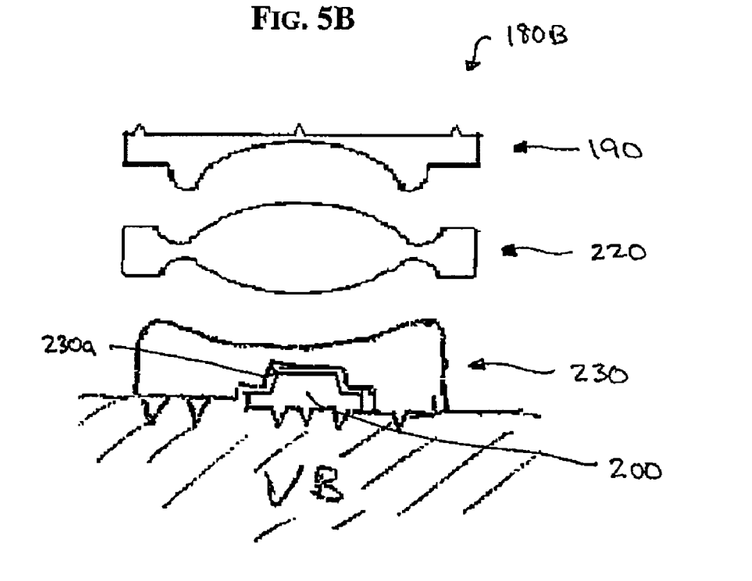
FIG. 5B is a cross-sectional side view of the first and second endplate components shown in FIG. 5A, and another embodiment of a central component for forming a modular disc prosthesis having a floating center of rotation.

FIGS. 5A and 5B illustrate another embodiment of a technique for mating two components. In this embodiment, the central component includes features to prevent rotation. The system in FIGS. 5A and 5B is similar to the system shown and described with respect to FIGS. 1A-2C and includes first and second endplate components 190, 200, a first central component 210 that is disposed between the first and second endplate components 190, 200 to form a disc prosthesis 180A having fixed center of rotation, and second and third central components 220, 230 that are disposed between the first and second endplate components 190, 200 to form a disc prosthesis 180B having a floating center of rotation. In this embodiment, the first and third central components 210, 230 are configured to extend around the endplate component 200 and to engage bone. In particular, each central component 210, 230 includes a cavity 210a, 230a formed therein and having a shape that complements a shape of the second endplate component 200, such that the cavity 210a, 230a of each central component 210, 230 can receive the entire endplate component 200 therein. As a result, a perimeter of each central component 210, 230 can extend around the endplate component 200 and contact the bone of the vertebra (labeled as VB). The central components 210, 230 can also include bone-engaging surface features, such as teeth 211, 231 as shown, to further prevent rotation of the central component 210, 230 relative to the vertebra, and also coatings (not shown), as previously described, to enhance bone engagement.

Figure 6A:
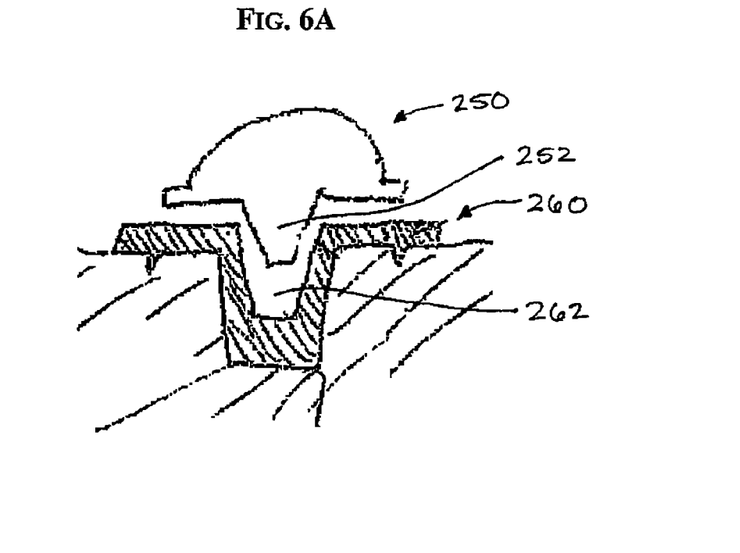
FIG. 6A is a cross-sectional side view a portion of another embodiment of a modular disc prosthesis system, showing an endplate component and a central component coupled by a post and bore connection.
Figure 6B:
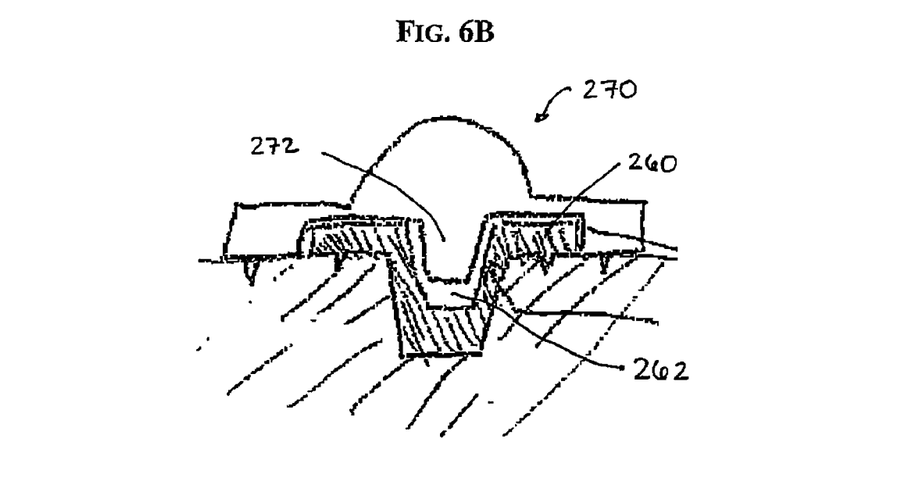
FIG. 6B is a cross-sectional side view a portion of another embodiment of a modular disc prosthesis system, showing an endplate component and a central component coupled by a post and bore connection.

In other embodiments, the post-and-bore connection can be reversed. FIGS. 6A and 6B illustrate another embodiment of a second endplate component 260 having a bore 262 formed therein for receiving a complementary post 252, 272 formed on a central member 250, 270. Central component 250 shown in FIG. 6A has a conical post 252 that extends into a conical bore 262, such that the central component 250 can rotate relative to the second endplate component 260. Central component 270 in FIG. 6B, on the other hand, extends around the endplate component 260 such that a perimeter of the central component 270 contacts an endplate of the vertebra to prevent rotation of the central component 270 relative to the endplate component 260.

Figure 6C:
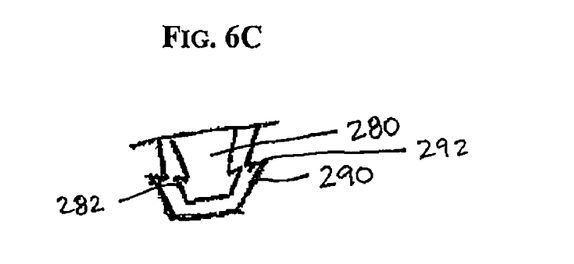
FIG. 6C is a cross-sectional side view of one embodiment of a post and bore connection.
Figure 7A:
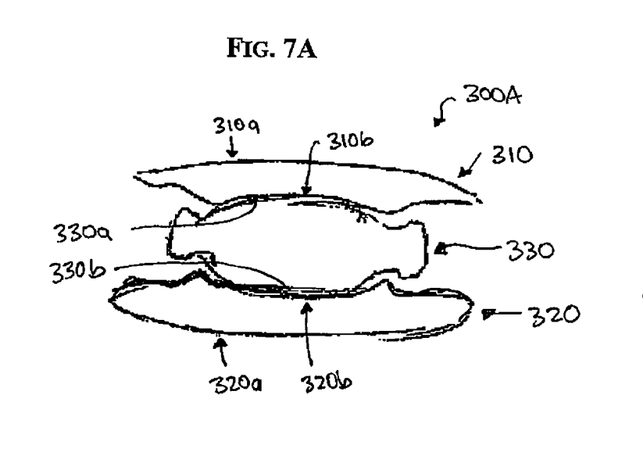
FIG. 7A is a cross-sectional side view of another embodiment of a modular disc prosthesis system, showing first and second endplate components and a central component configured to be disposed between the endplate components to form a disc prosthesis having a floating center of rotation.
Figure 7B:
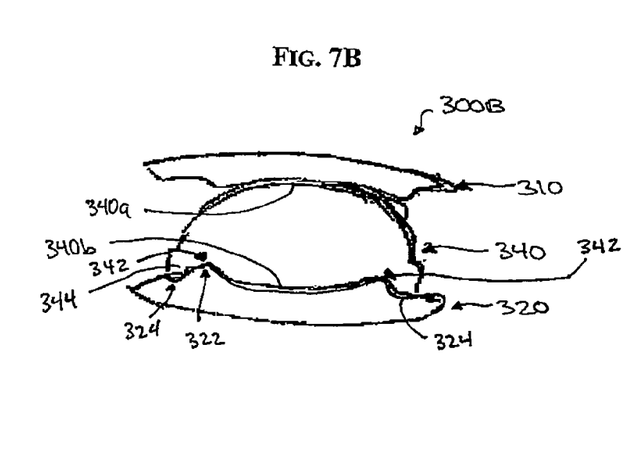
FIG. 7B is a cross-sectional side view of the first and second endplate components of FIG. 7A, and another embodiment of a central component configured to be disposed between the endplate components to form a disc prosthesis having a fixed center of rotation.
Figure 7C:
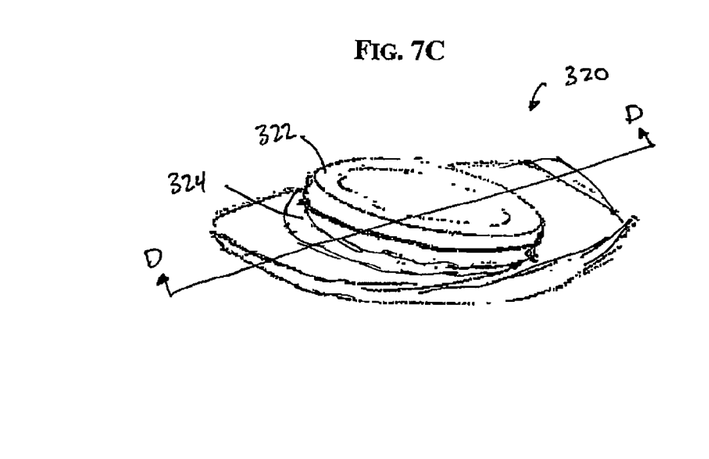
FIG. 7C is a top perspective view of the second endplate component of FIGS. 7A and 7B.
Figure 7D:
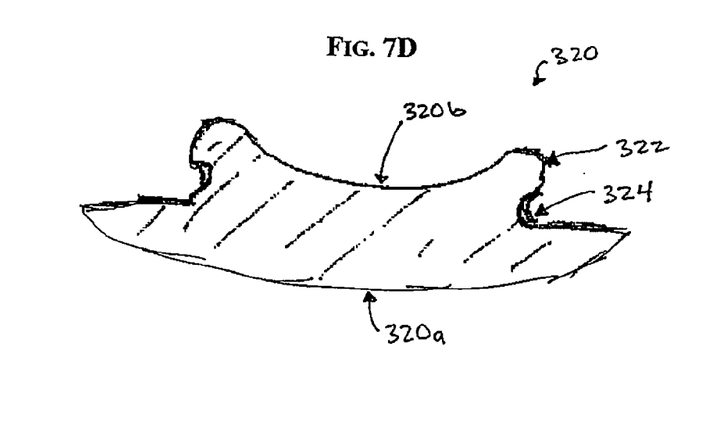
FIG. 7D is a cross-sectional side view taken across line D-D of the second endplate component shown in FIG. 7C.

In other embodiments, the post-and-bore connection can include positive mating features such that the post and bore engage one another. FIG. 6C illustrates one exemplary embodiment of a technique for positively mating a post and bore. As shown, the post 280 has an enlarged head or flange 282 formed thereon, and the bore 290 includes a corresponding recess or groove 292 formed therein for seating the head or flange 282 on the post 280. As a result, when the post 280 is inserted into the bore 290, the flange 282 will extend into and engage the groove 292, thereby preventing the post 280 from backing out of the bore 280. A person skilled in the art will appreciate that a variety of other mating techniques can be used, for example, an interference fit, a press-fit, a snap-fit, a threaded connection, etc.

FIGS. 7A-7D illustrate another exemplary embodiment of a modular disc replacement system. In this embodiment, the system includes first and second endplate components 310, 320, and two interchangeable central components 330, 340. The first central component 330 is configured to form a disc prosthesis 300A having a floating center of rotation, and the second central component 340 is configured to form a disc prosthesis 300B having a fixed center of rotation.

Each endplate component 310, 320 can have a variety of configurations, but each endplate component 310, 320 preferably includes a bone-contacting surface 310a, 320a and an opposed articular or mating surface 310b, 320b. The bone-contacting surfaces 310a, 320a can have virtually any shape and size, and can include various features formed thereon to facilitate mating and/or positioning of each endplate component 310, 320 adjacent to a vertebral endplate. The mating or articular surfaces 310b, 320b can also vary in shape and size, but they are preferably adapted to allow each central component 330, 340 to be received therebetween, and to allow the first central component 330 to move relative to both endplate components 310, 320, while allowing the second central component 340 to move relative to only one of the endplate components, e.g., the first endplate component 320. While various techniques can be used to achieve such a configuration, in the illustrated embodiment each endplate component 310, 320 includes a substantially concave cavity formed therein for seating a complementary substantially convex surface 330a, 340a, 330b, 340b formed on each central component 330, 340. At least one of the endplate components, e.g., the second endplate component 320, can also include a mating feature formed thereon and configured to mate with a complementary mating feature formed on the second central component 340. While various mating techniques can be used, in the illustrated embodiment the second endplate component 320 includes a raised ridge 322 that defines the substantially concave cavity 340b, and a groove 324 formed around the ridge 322. The ridge 322 and groove 324 are shown in more detail in FIGS. 7C and 7D. The second central component 340 includes a complementary groove 342 for seating the raised ridge 322 on the second endplate component 320, and a complementary ridge 344 that extends into the groove 324 on the second endplate component 320. As a result, the second central component 340 and the second endplate component 320 will engage and mate to one another, thus forming a disc prosthesis with a fixed center of rotation. Such a configuration is particularly advantageous as the disc prosthesis only requires four components. However, the components can optionally be provided as a kit having multiple shapes and sizes of each component.

Figure 8:
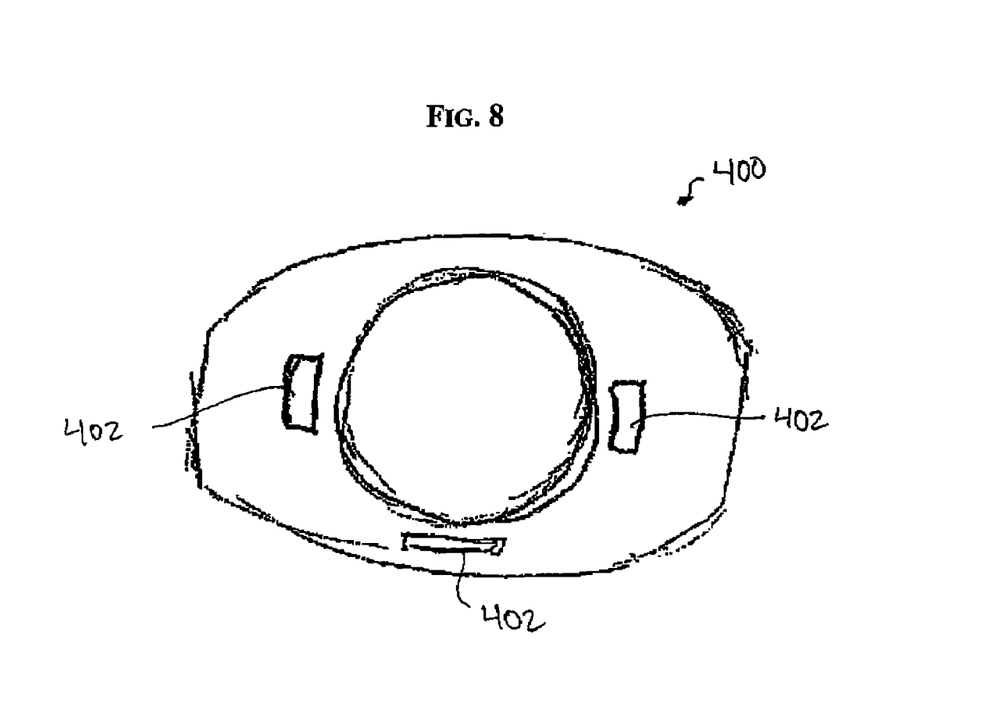
FIG. 8 is a top view of another embodiment of an endplate component for use in a modular disc prosthesis system.
Figure 9:
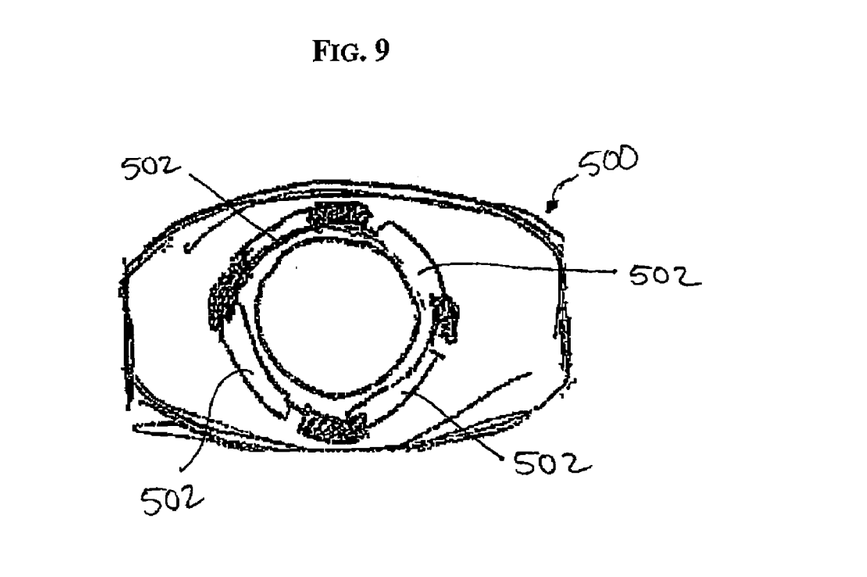
FIG. 9 is a top view of another embodiment of an endplate component for use in a modular disc prosthesis system.

While FIGS. 7A-7D illustrate a tongue-and-groove type mating connection between the second central component 340 and the second endplate component 320, various other mating techniques can be used. For example, FIG. 8A illustrates an endplate component 400 having several slots 402 formed therein. The slots 402 are configured to received corresponding legs or protrusions formed on the central component (not shown). The legs or protrusions can be configured to snap into the slots 402 to mate the two components. FIG. 9 illustrates another embodiment of a mating technique that can be used to mate two components. In this embodiment, the endplate component 500 utilizes a twist-lock connection. In particular, the endplate component 500 includes several flanges 502 formed thereon and spaced apart from one another. The central component (not shown) can also include several flanges that can be positioned between the flanges 502 on the endplate component. The central component can then be rotated such that the flanges 502 on the endplate component engage the flanges on the central component, thereby mating the two components to one another. A person skilled in the art will appreciate that various other twist-lock mechanisms can be used, and that the various mating connections disclosed herein can be reversed. Moreover, a variety of other mating techniques known in the art can be used, such as threads, a snap-fit connection, an interference fit connection, a tongue-and-groove connection, a post-and-bore connection, and a press-fit connection.

In another exemplary embodiment, a modular disc replacement system can be provided as a kit having one or more of each components. The components can vary with respect to configuration, as well as size. For example, each endplate component can be provided in multiple shapes and/or sizes to allow a surgeon to select a size that is appropriate for the patient. The central components can likewise be provided in multiple shapes and/or sizes to meet the particular patient's needs.

The present invention also provides methods and devices for optimizing a desired position of the center of rotation of a modular disc prosthesis. This is particularly useful in situations where it is desirable to have an offset center of rotation while still positioning the endplate components centrally relative to the vertebral endplate to maximize bone contact, or to correct for an endplate that is positioned offset from the center of the vertebral endplate without disrupting the interface already established by the surgical placement of the endplate component on the vertebral endplate. The correction can be predetermined pre-operatively, or it can be determined intra-operatively. In an exemplary embodiment, one or more components of the various modular disc prostheses disclosed herein can have a predetermined offset to allow the center of rotation to be positioned at a desired location relative to the vertebral endplates. For example, the endplate component or central component in any of the previously described embodiments can be provided in a kit containing a plurality of endplate or central components. The plurality of components can each have a predetermined offset, with the offsets differing from one another. In use, the component having the desired offset can be selected to achieve the desired result. Thus, in the embodiments shown in FIGS. 1A-9, a plurality of endplate and/or central components can be provided having a mating surface that is offset from an opposed bone-contacting or mating surface. As a result, when the disc prosthesis is assembled, the endplate components can be misaligned with one another, however the center of rotation can be located as desired relative to the vertebral endplates. Such a configuration provides the surgeon with flexibility to optimize the position of the center of rotation of the disc prosthesis by merely selecting the appropriate components.

Exemplary methods for implanting a modular disc replacement system are also provided. While various techniques known in the art can be used to implant a modular disc replacement system, in an exemplary embodiment the damaged disc is first removed and the end surfaces of the exposed vertebrae are cleared of debris. The vertebrae are distracted and first and second endplate components having the desired configuration are then positioned on the respective vertebra and tapped into place. The central components can be selected pre- or intra-operatively to construct an implant having a desired constraint or degree of freedom. Once selected, the central components can be inserted between the endplate components to form the disc prosthesis. The vertebrae are then returned to their normal position, whereby the pressure of the spinal column will further seat the endplate components into the vertebral bones and will secure the central component(s) therebetween. Depending on the selected components, the disc prosthesis will allow a particular degree of freedom between the adjacent vertebrae.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A modular intervertebral disc prosthesis system, comprising:
   a core component and a plurality of interchangeable components adapted to movably couple to the core component, the plurality of interchangeable components including a first component being configured to movably couple to the core component to form a disc prosthesis having a fixed center of rotation, a second component being configured to movably couple to the core component to form a disc prosthesis having a floating center of rotation, an endplate component configured to be positioned adjacent to an endplate of a vertebrae, and a third component configured to be disposed between the second component and the endplate component and configured to move relative to the second component and to mate to the endplate component to prevent movement between the third component and the endplate component.

2. The system of claim 1, wherein the endplate component comprises a first endplate component and the core component comprises a second endplate component adapted to be positioned adjacent to a vertebral endplate and.

3. The system of claim 2, wherein the first endplate component includes a bone-contacting surface adapted to be positioned adjacent to an endplate of a vertebra, and an opposed mating surface adapted to mate to at least one of the first component and the third component.

4. The system of claim 3, wherein the
   second and third components are adapted to be movably disposed between the first and second endplate components to form a disc prosthesis having a floating center of rotation, the third component being adapted to mate to the first endplate component, and
   wherein the first component is interchangeable with the second and third components and is adapted to be movably disposed between the first and second endplate components to form a disc prosthesis having a fixed center of rotation.

5. The system of claim 4, wherein the second component includes a first substantially convex surface adapted to be movably seated within a corresponding substantially concave surface formed in the second endplate component, and an opposed substantially convex surface adapted to be movably seated within a corresponding substantially concave surface formed in the third component.

6. The system of claim 4, wherein the third component and the first endplate component are adapted to mate using a connection selected from the group consisting of a snap-fit, an interference fit, a tongue-and-groove, a post-and-bore, and a press-fit.

7. The system of claim 4, wherein the first component includes a substantially convex surface adapted to be received within a corresponding substantially concave surface formed in the second endplate component, and an opposed mating surface adapted to mate to a complementary mating surface formed on the first endplate component.

8. The system of claim 7, wherein the first component and the first endplate component are adapted to mate using a connection selected from the group consisting of a snap-fit, an interference fit, a tongue-and-groove, a post-and-bore, and a press-fit.

9. The system of claim 2, wherein the plurality of interchangeable components includes
   a third endplate component, the first and third endplate components being interchangeable and being adapted to be positioned adjacent to an endplate of a vertebra, and
   a fourth component adapted to be movably disposed between the second endplate component and third endplate component.

10. The system of claim 9, wherein the second endplate component includes a bone-contacting surface adapted to be positioned adjacent to an endplate of a vertebra, and an opposed surface having a substantially convex cavity formed therein, and the third endplate component includes a bone-contacting surface adapted to be positioned adjacent to en endplate of a vertebra, and an opposed surface having a substantially convex cavity formed therein.

11. The system of claim 1, wherein the first component includes an undercut formed around a perimeter thereof and adapted to receive and engage a corresponding ridge formed on the second endplate component to prevent movement between the first component and the second endplate component.

12. The system of claim 1, wherein the first component includes a plurality of protrusions formed thereon and adapted to extend into and engage corresponding bores formed in the endplate component to prevent movement between the second central component and the endplate component.

13. The system of claim 1, wherein the first component is adapted to rotate into a locked position to engage the endplate component to prevent movement between the first component and the endplate component.

14. A modular intervertebral disc prosthesis kit, comprising:

at least three components adapted to couple to one another and including a first endplate component configured to be positioned adjacent to a first endplate of a first vertebra, a second endplate component configured to be positioned adjacent to a second endplate of an adjacent second vertebra, a plurality of cores configured to be interchangeably disposed between the first and second endplate components to allow a first disc prosthesis to be formed having a fixed center of rotation, and a second disc prosthesis to be formed having a floating center of rotation.

15. The kit of claim 14, wherein the plurality of cores includes a first core adapted to be freely movably disposed between the first and second endplate components, and a second core adapted to be disposed between the first and second endplate components and adapted to move freely relative to the first endplate component and to engage the second endplate component to prevent movement between the second core and the second endplate component.

16. The kit of claim 14, wherein the plurality of cores includes first and second cores adapted to be movably disposed between the first and second endplate components to form a disc prosthesis having a floating center of rotation, and a third core adapted to be disposed between the first and second endplate components to form a disc prosthesis having a fixed center of rotation.

17. The kit of claim 16, wherein the first core has a post formed thereon for mating with a bore formed in the second endplate component, and a substantially concave surface for seating a complementary substantially convex surface formed on the second core, and the third core has a post formed thereon for mating with a bore formed in the second endplate component, and a substantially convex surface adapted to be movably received within a complementary concave surface formed in the first endplate component.

18. The kit of claim 14, wherein each component includes a first surface and a second, opposed surface, at least one of the surfaces being a mating surface configured to mate with a mating surface formed on another one of the components.

19. A modular intervertebral disc prosthesis system, comprising:

a first endplate component having a bone-contacting surface configured to be positioned adjacent to an endplate of a vertebra;

a second endplate component having a bone-contacting surface configured to be positioned adjacent to an endplate of a vertebra;

first and second central components disposable between the first and second endplate components to form a disc prosthesis having a floating center of rotation, the second central component being configured to mate to the second endplate component and the first central component being freely movable relative to the second central component and the first endplate component; and a third central component interchangeable with the first and second central components and disposable between the first and second endplate components to form a disc prosthesis having a fixed center of rotation.

20. The system of claim 19, wherein the third central component is freely movable relative to the first endplate component and fixed relative to the second endplate component.

21. The system of claim 19, wherein the third central component includes a first articular surface and an opposed generally planar surface.

22. The system of claim 19, wherein the first central component is freely movable relative to the first endplate component.

23. The system of claim 19, wherein the first central component includes opposed articular surfaces.

24. The system of claim 19, wherein the second central component includes a generally planar surface and an opposed concave surface for receiving an articular surface.

25. The system of claim 19, wherein the first endplate component includes a concave surface configured for receiving an articular surface.

26. The system of claim 19, wherein the second endplate component includes a generally planar surface configured for receiving one of the second central component and the third central component.

27. The system of claim 19, further comprising a third endplate component interchangeable with the second endplate component and configured to form a disc prosthesis having a floating center of rotation with the first endplate component and the first central component.

* * * * *